United States Patent
Shirahata et al.

(10) Patent No.: US 7,801,346 B2
(45) Date of Patent: Sep. 21, 2010

(54) MEDICAL IMAGE DISPLAY DEVICE, METHOD, AND PROGRAM

(75) Inventors: Takashi Shirahata, Chiba (JP); Yudai Ogawa, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 851 days.

(21) Appl. No.: 11/663,682

(22) PCT Filed: Sep. 22, 2005

(86) PCT No.: PCT/JP2005/017446

§ 371 (c)(1),
(2), (4) Date: Mar. 23, 2007

(87) PCT Pub. No.: WO2006/033377

PCT Pub. Date: Mar. 30, 2006

(65) Prior Publication Data

US 2007/0293755 A1    Dec. 20, 2007

(30) Foreign Application Priority Data

Sep. 24, 2004    (JP) ............................. 2004-276576

(51) Int. Cl.
  *G06K 9/00* (2006.01)
  *A61B 6/00* (2006.01)
(52) U.S. Cl. ............................. 382/128; 382/154; 378/21
(58) Field of Classification Search ................. 382/100, 382/128, 129, 130, 131, 132, 133, 134, 154, 382/168, 181, 189–199, 214, 232, 254, 274, 382/276, 285, 305; 600/407; 378/24, 26, 378/65, 21

See application file for complete search history.

(56) References Cited

U.S. PATENT DOCUMENTS

| 5,754,623 | A  | * | 5/1998  | Seki .............................. 378/65 |
| 6,901,277 | B2 | * | 5/2005  | Kaufman et al. ............. 600/407 |
| 7,130,457 | B2 | * | 10/2006 | Kaufman et al. ............. 382/128 |
| 7,245,754 | B2 | * | 7/2007  | Goto ........................... 382/128 |
| 7,298,878 | B2 | * | 11/2007 | Goto ........................... 382/128 |
| 7,369,691 | B2 | * | 5/2008  | Kondo et al. ................. 382/128 |

FOREIGN PATENT DOCUMENTS

| JP | 2001-14484  | 1/2001  |
| JP | 2002-245487 | 8/2002  |
| JP | 2002-336255 | 11/2002 |
| JP | 2004-8350   | 1/2004  |

* cited by examiner

*Primary Examiner*—Seyed Azarian
(74) *Attorney, Agent, or Firm*—Cooper & Dunham LLP

(57) ABSTRACT

A medical image display device includes: tomogram input means for inputting a plurality of tomograms obtained by a medical imaging device; 3-dimensional image construction means for constructing a 3-dimensional image by layering the tomograms inputted; arbitrary cross section image construction means for cutting the 3-dimensional image at an arbitrary cross section and constructing the cross section image from the tomograms; superimposed image construction means for constructing a superimposed image of the 3-dimensional image and the arbitrary cross section image according to positional information on the tomogram; and display means for displaying the superimposed image thus constructed.

17 Claims, 14 Drawing Sheets

MEDICAL IMAGE DISPLAY DEVICE, METHOD, AND PROGRAM

TECHNICAL FIELD

The present invention relates to a technique for obtaining a tomogram of a subject from a medical image diagnosis device (modality) including X-ray CT device, MRI device and ultrasound device, and capable of simultaneously displaying 3-dimensional configuration of the obtained observation target organ and positional relationship between the observation target organ and the surrounding organs.

The present application accompanies the claim of priority in Paris, based on Japanese Patent Application No. 2004-276576 by Japanese Patent Law, and is to be incorporated by reference for receiving the benefit of Japanese Patent Application No. 2004-276576.

BACKGROUND ART

For example, upon performing examination of organs with motion such as a heart, it is possible to diagnose abnormal motional state such as calcification of cardiac muscle or infarction of the heart through displaying the measurement result in real time. Imaging and display in real time is now practically applied in images such as two-dimensional tomograms of a heart.

Recently the analysis of organs with motion by 3-dimensional images have been attempted since the form of organs sequentially changes and it is hard to grasp the entire configuration of organs with motion only by 2-dimensional image.

However, construction of a 3-dimensional image of organs with motion requires a large amount of data to be calculated, thus the technique for real-time display has not been established in spite of current state of computers with high-speed calculation.

Given this factor, a work around method has been provided which is for displaying a 3-dimensional image of an organ-region and a cross-section of an arbitrary position side-by-side, obtaining a 3-dimensional configuration of an organ and information of the cross-sectional image, and adding information on the 3-dimensional depth direction on the 2-dimensional image of the cross-sectional image (for example, Patent Document 1).

Patent Document 1: JP-A-2000-107182

DISCLOSURE OF THE INVENTION

Problems to be Solved

However, in Patent Document 1, the invention lacks the idea of displaying 3-dimensional configuration of a target region from arbitrary directions and information on surrounding organs hidden in the 3-dimensional image simultaneously.

The objective of the present invention, therefore, is to provide a medical image display device, method and program capable of displaying 3-dimensional configuration of a target region from arbitrary directions and information on surrounding organs hidden in the 3-dimensional image simultaneously.

Means for Solving the Problems

A medical image display device of the present invention comprises:
  tomogram input means for inputting a plurality of tomograms obtained by a medical imaging device;
  3-dimensional image construction means for constructing a 3-dimensional image by layering the tomograms inputted;
  arbitrary cross-section image construction means for cutting the 3-dimensional image at an arbitrary cross-section and constructing the cross-section image from the plurality of tomograms;
  superimposed image construction means for constructing an superimposed image of the 3-dimensional image and the arbitrary cross-section image according to positional information on the tomogram; and
  display means for displaying the superimposed image thus constructed.

A medical image display method of the present invention includes:
  a tomogram input step for inputting a plurality of tomograms obtained by a medical imaging device;
  a 3-dimensional image construction step for constructing a 3-dimensional image by layering the tomograms inputted;
  an MPR image construction step for cutting the 3-dimensional image at an arbitrary cross-section and constructing the cross-section from the tomograms;
  a superimposed image construction step for constructing an superimposed image of the 3-dimensional image and the arbitrary cross-section image according to positional information on the tomogram;
  a display step for displaying the superimposed image thus constructed.

A medical image display program of the present invention run on a computer includes:
  a tomogram input process for inputting a plurality of tomograms obtained by a medical imaging device;
  a 3-dimensional image construction process for constructing a 3-dimensional image by layering the tomograms inputted;
  an MPR image construction process for cutting the 3-dimensional image at an arbitrary cross-section and constructing the cross-section from the tomograms;
  a superimposed image construction process for constructing a superimposed image of the 3-dimensional image and the arbitrary cross-section image according to positional information on the tomogram;
  a display process for displaying the superimposed image thus constructed.

Effect of the Invention

In accordance with the present invention, information on the 3-dimensional configuration from arbitrary directions and information on the surrounding region hidden in the 3-dimensional image can be displayed simultaneously.

DESCRIPTION OF THE SYMBOLS

10 . . . CPU, 11 . . . medical tomogram imaging device, 12 . . . LAN, 13 . . . magnetic disk, 14 . . . main memory, 15 . . . controller, 16 . . . mouse, 17 . . . keyboard, 18 . . . display memory, 19 . . . display.

BEST MODE FOR CARRYING OUT THE INVENTION

Figure 1:
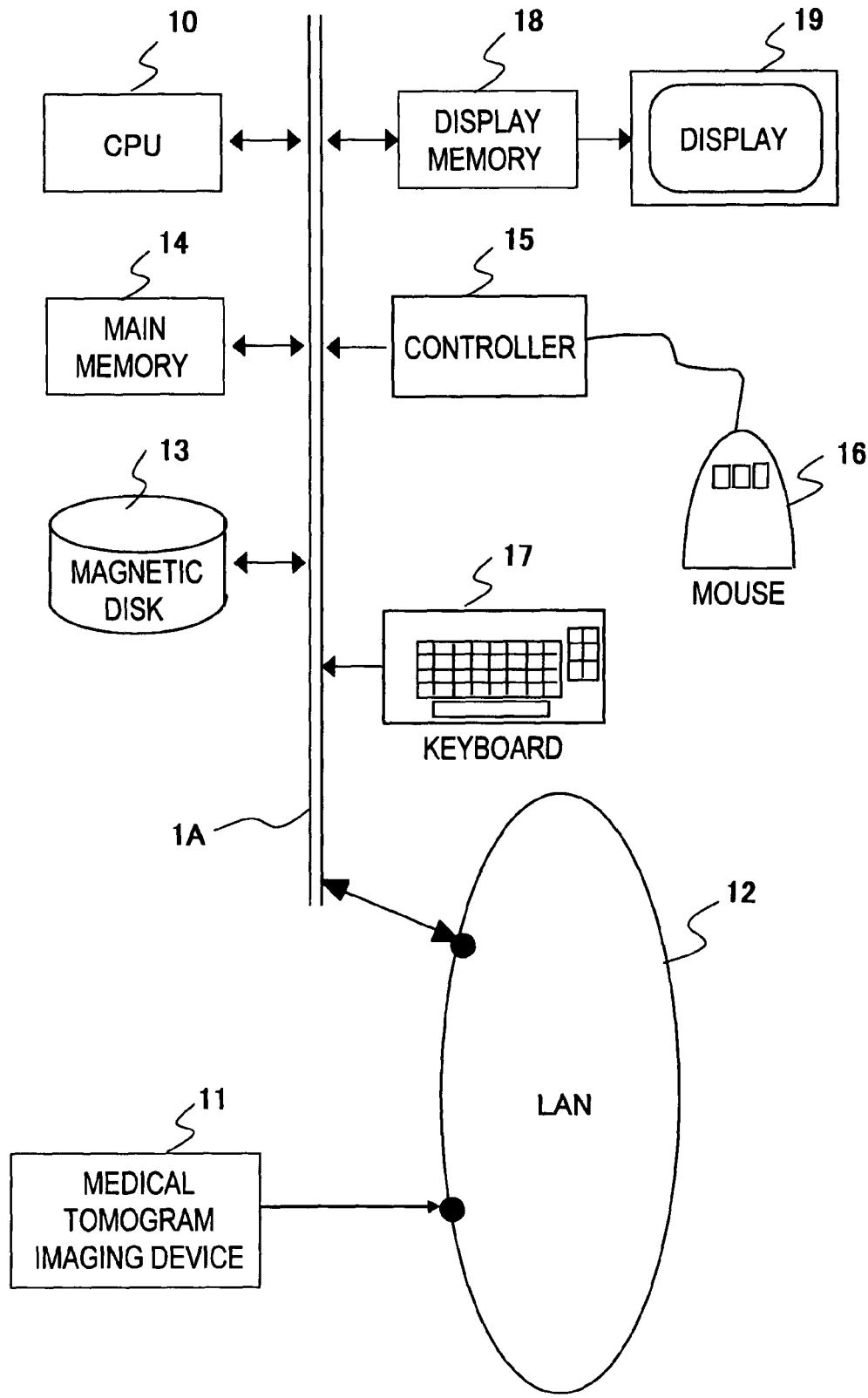
FIG. 1 is an example of a medical image display device by the present invention.

A medical image display method, medical image display program and medical image display device of the present invention are carried out by such a computer system illustrated in FIG. 1.

As for the diagrams to be used for the description of the present embodiment, the parts having the same function are encoded with the same codes, and the repeated descriptions are omitted.

The computer system is provided with CPU 10, magnetic disk 13 connected via CPU 10 and data transfer bus 1A, main memory 14, controller 15 and display memory 18.

CPU 10 is for executing the calculation for region extraction or the calculation for constructing the projection image. Magnetic disk 13 is for receiving the medical tomograms imaged by medial imaging device 11 via network such as LAN 12 and storing them. Main memory 14 is for storing the medical tomogram data or intermediate steps of calculation while calculating for the region extraction. Controller 15 is provided with mouse 16 or keyboard 17 connected for inputting the starting point for the extraction or parameters necessary for region extraction, and an operator inputs information such as parameters using mouse 16 or keyboard 17. Display device 19 has units such as display memory 18 to use for displaying the results of region extraction, a liquid crystal display or CRT.

Figure 2:
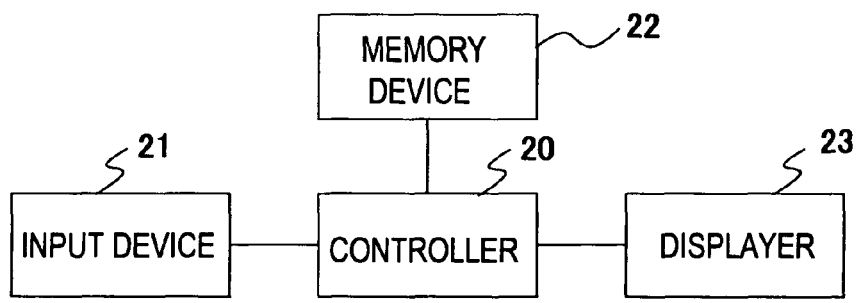
FIG. 2 is a block diagram of a major part abstracted from FIG. 1.
Figure 3:
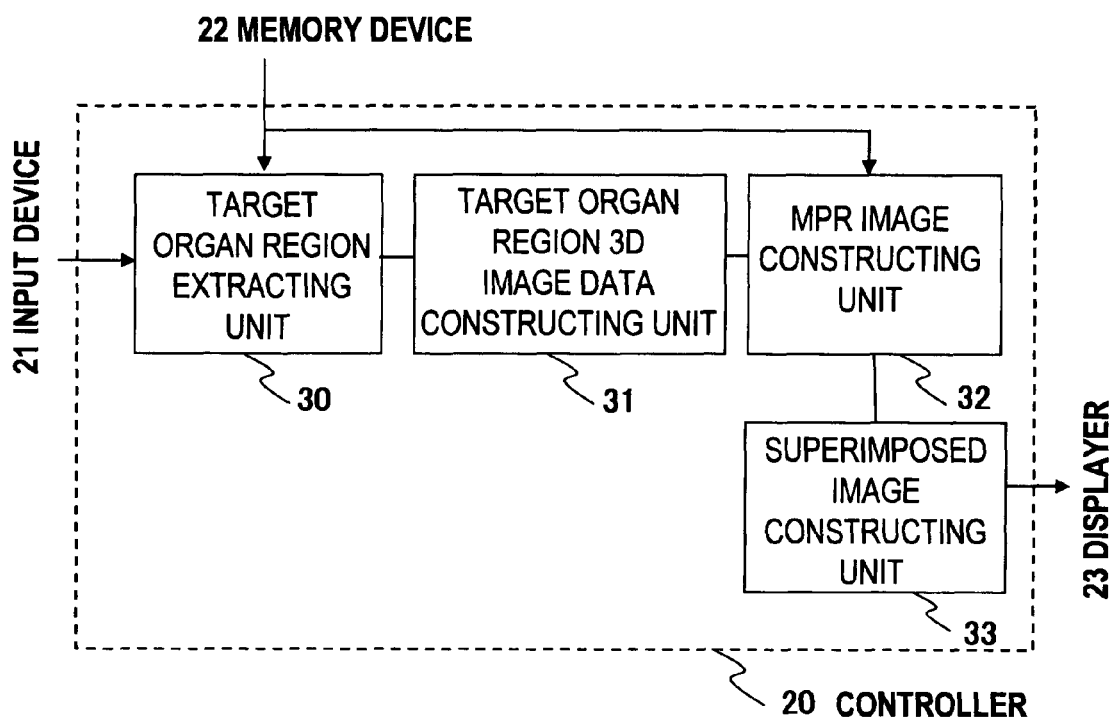
FIG. 3 is a detail of controller 20 in FIG. 2.

FIG. 2 is a functional block diagram of FIG. 1, and FIG. 3 is the detail of controller 20 in FIG. 2. The computer system is provided with input device 21, memory device 22, and controller 20 connected with displayer 23.

Controller 20 comprises target organ region extracting unit 30 connected to input device 21 and memory device 22, 3-dimensional image data construction device 31 regarding the target region, MPR image construction unit 32 and superimposed image construction unit 33. The medical image display device of the present invention is operated by the method according to the procedure in the flow chart shown in the respective embodiments through the program carried out by a computer.

Figure 4:
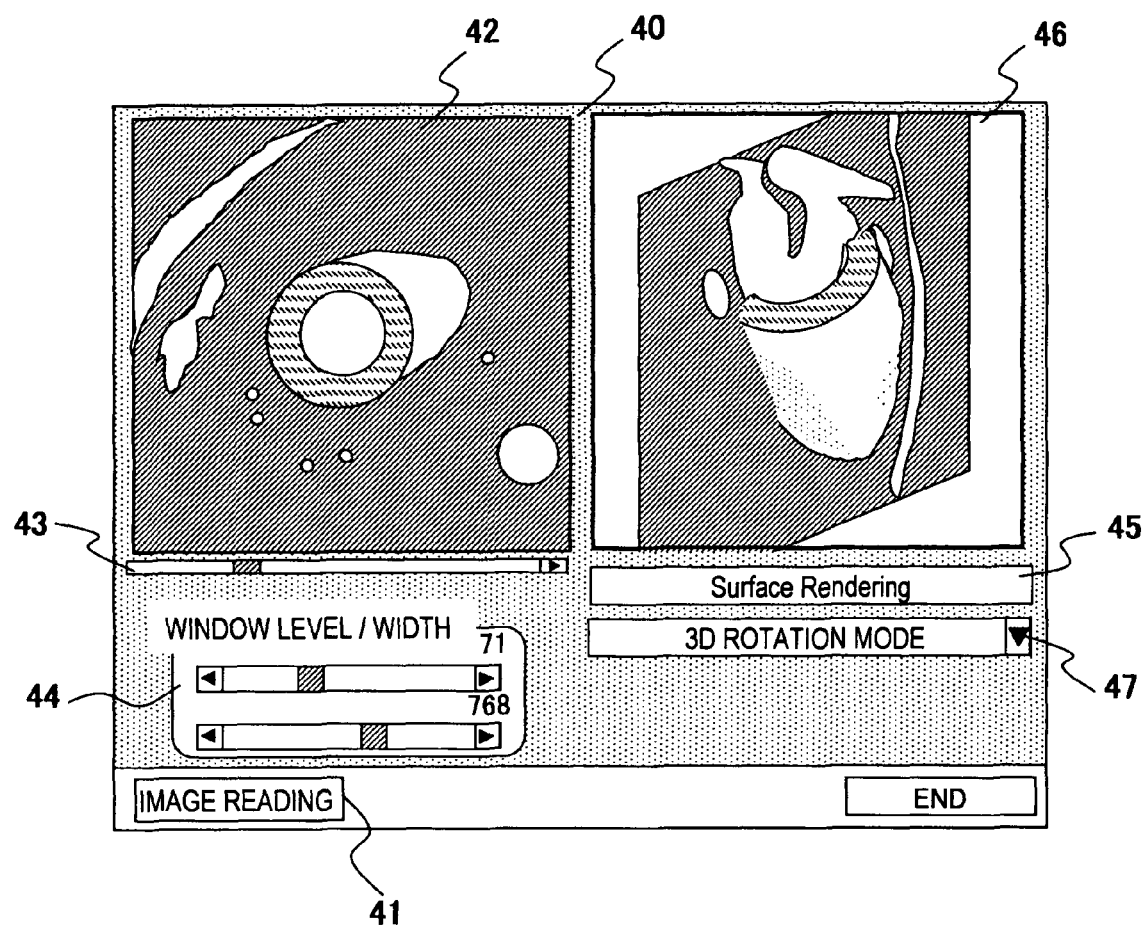
FIG. 4 is an example of GUI for implementing embodiment 1.
Figure 5:
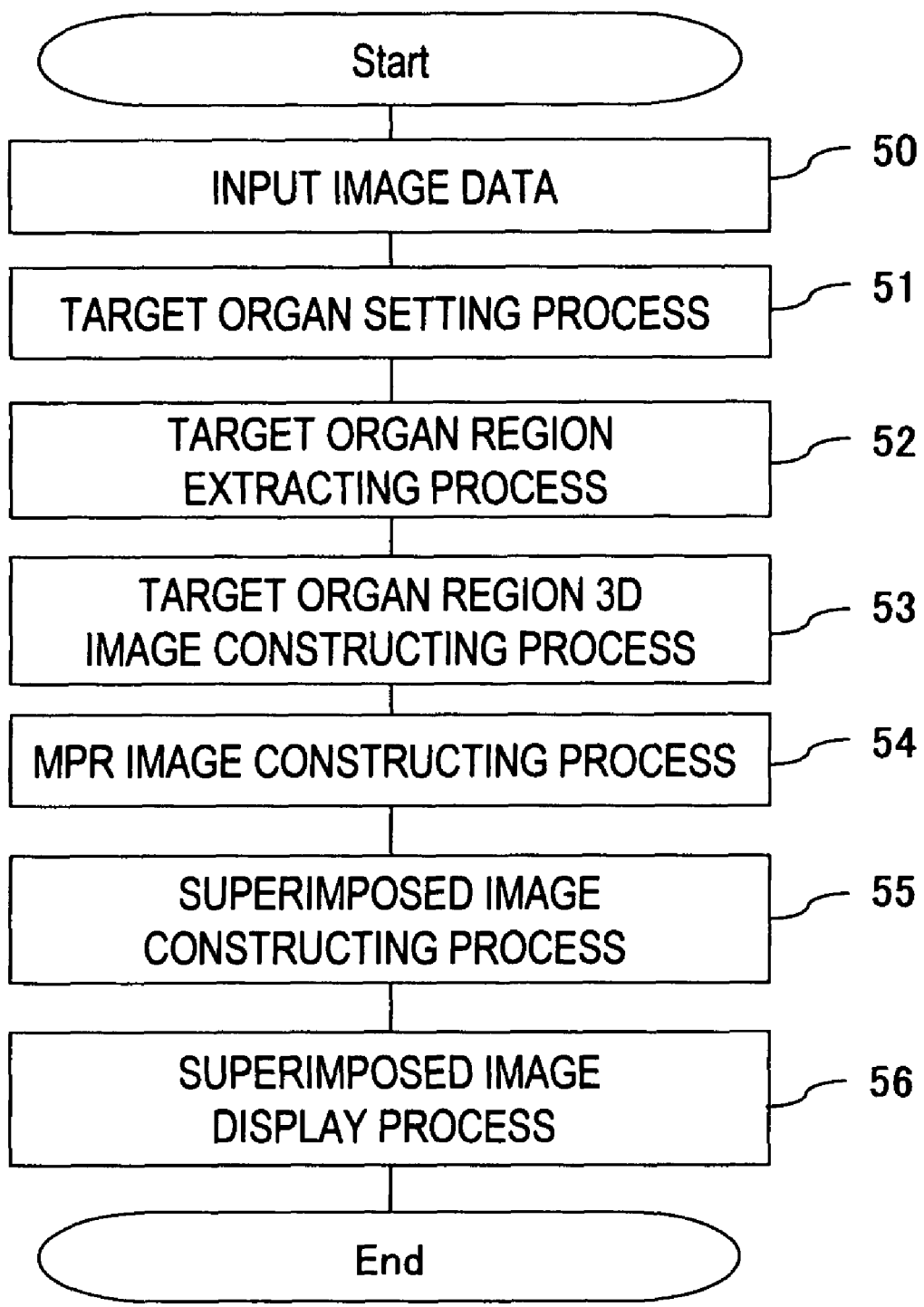
FIG. 5 is an example of a processing flowchart of embodiment 1.

First embodiment of the present invention will now be described using the diagrams. FIG. 4 shows an example of the graphical user interface (GUI) for implementing the first embodiment. An example of the processing flow chart in the first embodiment is shown in FIG. 5. The respective steps of FIG. 5 will be described below. The present embodiment exemplifies the case that a cardiac muscle is cited as the target organ.

(Step 50)

The operator inputs a group of medical tomograms imaged by X-ray CT device or MRI device by operating image read-in button 41 of GUI 40 using an input device such as mouse 16. The inputted images are displayed on image display region 42. The slice of image to be displayed out of the inputted medical tomogram group may be selected at the discretion of the operator through operating slice-forwarding scroll bar 43 using an input device such as mouse 16 or keyboard 17.

Also, the operator can display the inputted images with the arbitrary gradation by operating gradation conversion scroll bar 44 using an input device such as mouse 16 or keyboard 17.

(Step 51)

The operator specifies the target organ region on a medial tomogram image such as an X-ray CT image or MR image being displayed on image display region 42 of GUI 40 by operating an input device such as mouse 16.

(Step 52)

CPU 10 extracts the specified organ region using the region extraction method (region growing method) disclosed in, for example, Japanese Patent No. 2845995.

(Step 53)

CPU 10 constructs a 3-dimensional image of the target organ region extracted in step 52, using a method such as the surface rendering method or volume rendering method. It may be set so that the operator can arbitrarily choose whether to use the surface rendering method or volume-rendering method by operating combo box 45 on GUI 40 using an input device such as mouse 16.

Figure 6:
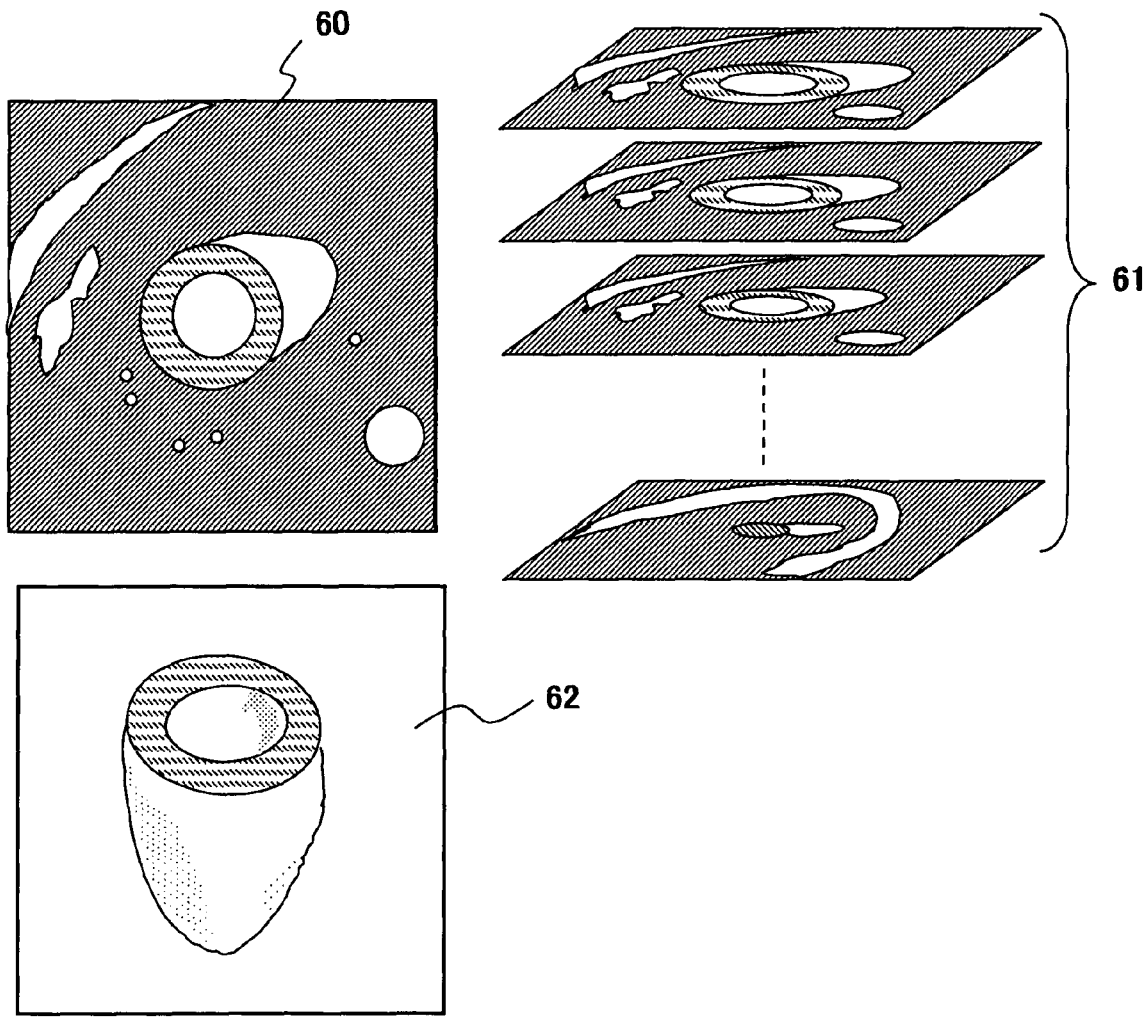
FIG. 6 is an example of a 3-dimensional image constructed in embodiment 1.

For example, image 62 in FIG. 6 is an example of the case that CPU 10 extracted the cardiac muscle as a target organ from image group 62 formed by image 60 of the cardiac muscle as shown in FIG. 6.

(Step 54)

Figure 7:
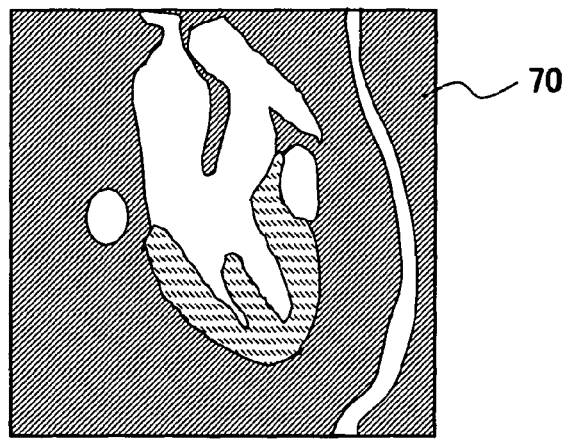
FIG. 7 is an example of an MPR image constructed in embodiment 1.

CPU 10 constructs an MPR image that is cut at the cross-section with a discretional slope and has the discretional coordinate in the superimposed medical tomographic images as a center. The MPR image is constructed, in the case that the cardiac muscle image group in FIG. 6 is applied, turns out to be, for example, as image 70 of FIG. 7.

(Step 55)

Figure 8:
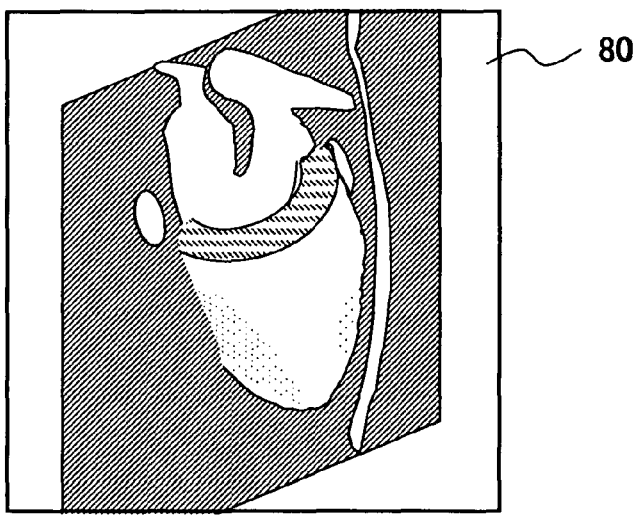
FIG. 8 is an example of a superimposed image of the 3-dimensional image and MPR image constructed in embodiment 1.

CPU 10 constructs a superimposed image of the 3-dimensional image of the target organ region and the MPR image. Here, the positional relationship of the 3-dimensional image and MPR image is made to coincide with the actual positional relationship by matching the coordinate. For example, an image like superimposed image 80 in FIG. 8 can be acquired from 3-dimensional image 62 in FIG. 6 and MPR image 70 in FIG. 7.

(Step 56)

CPU 10 displays the constructed superimposed image of the 3-dimensional image and MPR image on superimposed image display region 46 on GUI 40.

Here, the angle of the displayed 3-dimensional image may be set so that the operator can freely change the angle by dragging mouse 16 on superimposed image display region 46. Upon rotation of the 3-dimensional image, the MPR image can be set to rotate at the same time maintaining the positional relationship. Or, it can be set so that the operator can rotate only the cross-section for constructing an MPR image while maintaining the display angle of the 3-dimensional image. When the cross-section rotates, the MPR image to be displayed naturally varies in compliance with the position of the cross-section. Or, it may be set so that the operator can move only the central position of the cross-section for constructing an MPR image by dragging mouse 16 on display region 46 of the superimposed image while maintaining the angle of the 3-dimensional image and the cross-section for constructing the MPR image. The displayed MPR image varies in compliance with the movement of the central position of the cross-section.

As to the options to be operated using a mouse such as the rotation of the 3-dimensional image, the rotation of the cross-section for constructing an MPR image and the movement of the cross-section for constructing the MPR image, it may be set so that only one option can be carried out, or that the operator can choose to switch modes such as the rotation or the movement and can carry out all of the options. These modes may be set as selective in, for example, rotation mode combo box 47 on GUI 40.

With such setting, observation of the 3-dimensional configuration of the target region from arbitrary directions and information on the surrounding organs of the 3-dimensional image can be obtained simultaneously.

Second Embodiment

Figure 9:
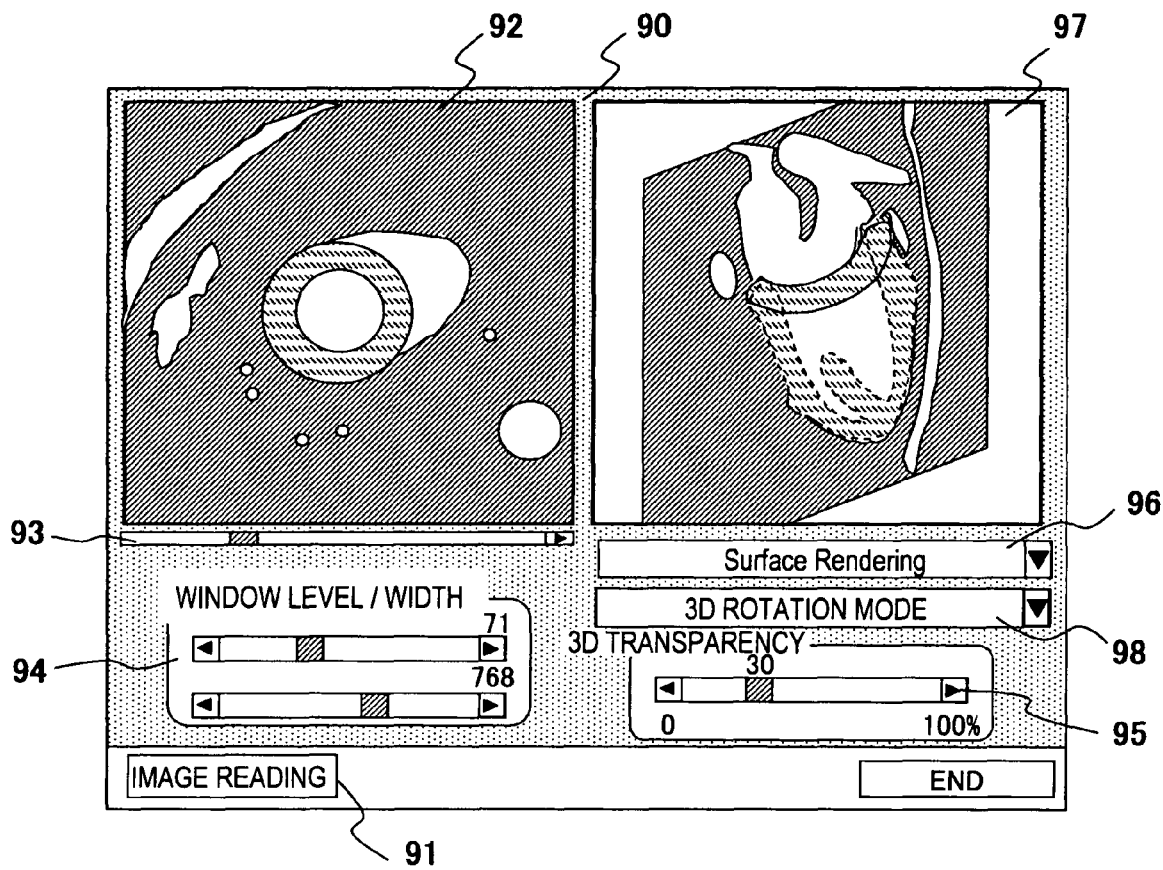
FIG. 9 is an example of GUI for implementing embodiment 2.
Figure 10:
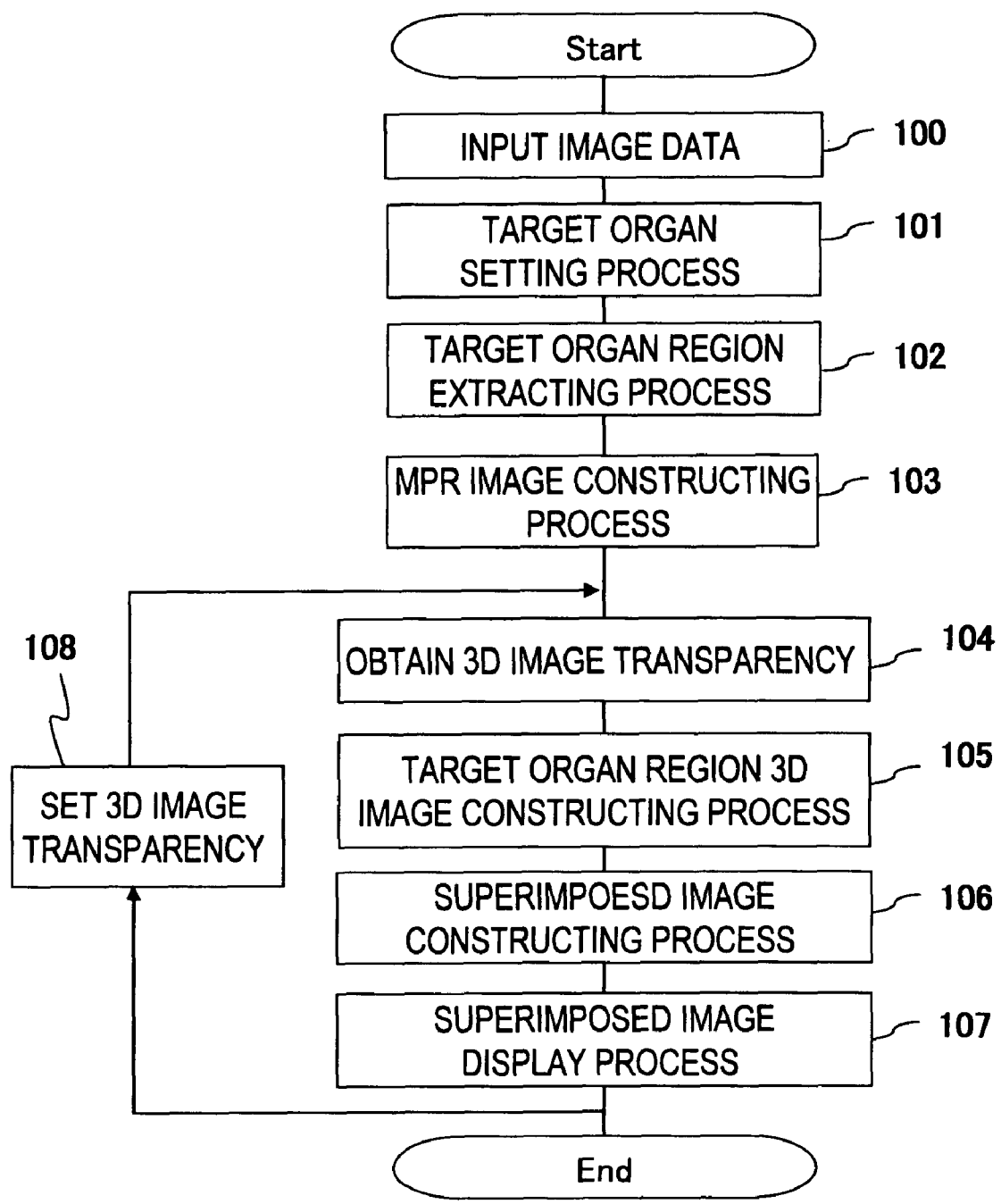
FIG. 10 is an example of processing flowchart of embodiment 2.

The second embodiment of the present invention will be described using the diagrams. An example of the GUI for implementing the present embodiment is shown in FIG. 9. An example of the processing flow chart of the present embodiment is shown in FIG. 10. The respective steps of FIG. 10 will be described below using a diagram.

(Step 100)

The operator inputs a medical tomogram group such as X-ray CT images or MR images imaged by X-ray CT apparatus or MRI apparatus by pushing image read-in button 91 of GUI 90 using an input device such as mouse 16. The inputted images are displayed on image display region 92. It may be set so that the operator can select the slice of image to display out of the inputted medical tomogram group by operating slice-forwarding scroll bar 93 using an input device such as mouse 16 or keyboard 17. It also may be set so that the operator can display the inputted images with arbitrary gradation through operating gradation-converting scroll bar 94 using an input device such as mouse 16 or keyboard 17.

(Step 101)

The operator specifies the organ region to be the observation target on a medical tomogram such as an X-ray CT image or MR image being displayed on image display region 92 of GUI 90 by operating an input device such as mouse 16.

(Step 102)

CPU 10 extracts the specified organ region using, for example, the region growing method.

(Step 103)

CPU 10 constructs an MPR image that is cut at the cross-section with a discretional slope and has the discretional coordinate in the superimposed medical tomographic images as a center.

(Step 104)

CPU 10 acquires the value of transparency from transparency-setting scroll bar 95.

Step 105)

CPU 10 constructs a 3-dimensional image of the organ region for the observation target extracted in step 102, using the surface rendering method or volume rendering method. It may be set so that the operator can freely change whether to use the surface rendering method or volume rendering method by operating combo box 96 on GUI 90 using an input device such as mouse 16.

(Step 106)

Figure 11:
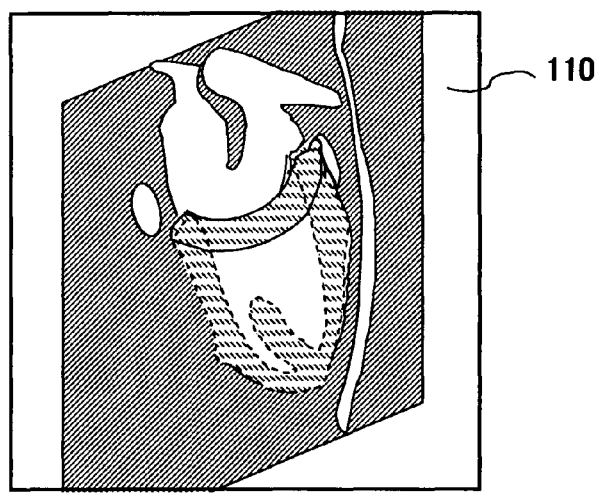
FIG. 11 is an example of a superimposed image of the 3-dimensional image and MPR image constructed in embodiment 2.

CPU 10 constructs a superimposed image of a 3-dimensional image of the target organ region and the MPR image. Then the coordinate is set so that the positional relationship between the 3-dimensional image and MPR image coincides with the actual positional relationship. Also, by superimposing the 3-dimensional image translucently displaying using transparency obtained in step 104, the superimposed image turns out as seen in image 110 of FIG. 11. By such operation, the 3-dimensional image is translucently displayed and the MPR image is displayed in transparent state.

(Step 107)

CPU 10 displays the superimposed image of the constructed 3-dimensional image and MPR image on superimposed image display region 97 on GUI 90.

Here, it may be set so that the operator can freely change the display angle of the 3-dimensional image by dragging mouse 16 on superimposed image display region 97. Upon rotation of the 3-dimensional image, the MPR image can be set to rotate at the same time maintaining the positional relationship. Or, it may be set so that the operator rotates only the cross-section for constructing an MPR image while maintaining the angle of the 3-dimensional image by dragging mouse 16 on display region 97 of the superimposed image. When the cross-section rotates, the displayed MPR image naturally varies in compliance with the position of the cross-section. Alternatively, it may also be set so that the operator moves only the central position of the cross-section for constructing an MPR image while maintaining the angle of the 3-dimensional image and the cross-section for constructing MPR image by dragging mouse 16 on display region 97 of the superimposed image. The displayed MPR image varies in compliance with the movement of the displayed MPR image.

As for the options to be operated using a mouse such as the rotation of the 3-dimensional image, the rotation of the cross-section for constructing an MPR image and the movement of the cross-section for constructing the MPR image, it may be set so that only one option can be carried out, or that the operator can choose to switch modes such as the rotation and can carry out all of the options. These modes may be set as selective in, for example, rotation mode combo box 98 on GUI 90.

(Step 108)

The operator may arbitrarily change transparency of the 3-dimensional image as necessary by operating transparency setting scroll bar 95 using an input device such as mouse 16 or keyboard 17 while observing the superimposed image displayed on superimposed image display region 97 on GUI 90.

In the 3-dimensional image construction process, step 104 is to proceed immediately when transparency of the 3-dimensional image is changed, and the new superimposed image is constructed.

Accordingly, information on both the 3-dimensional image set as translucent and the MPR image can be obtained simultaneously by superimposing them.

Embodiment 3

Figure 12:
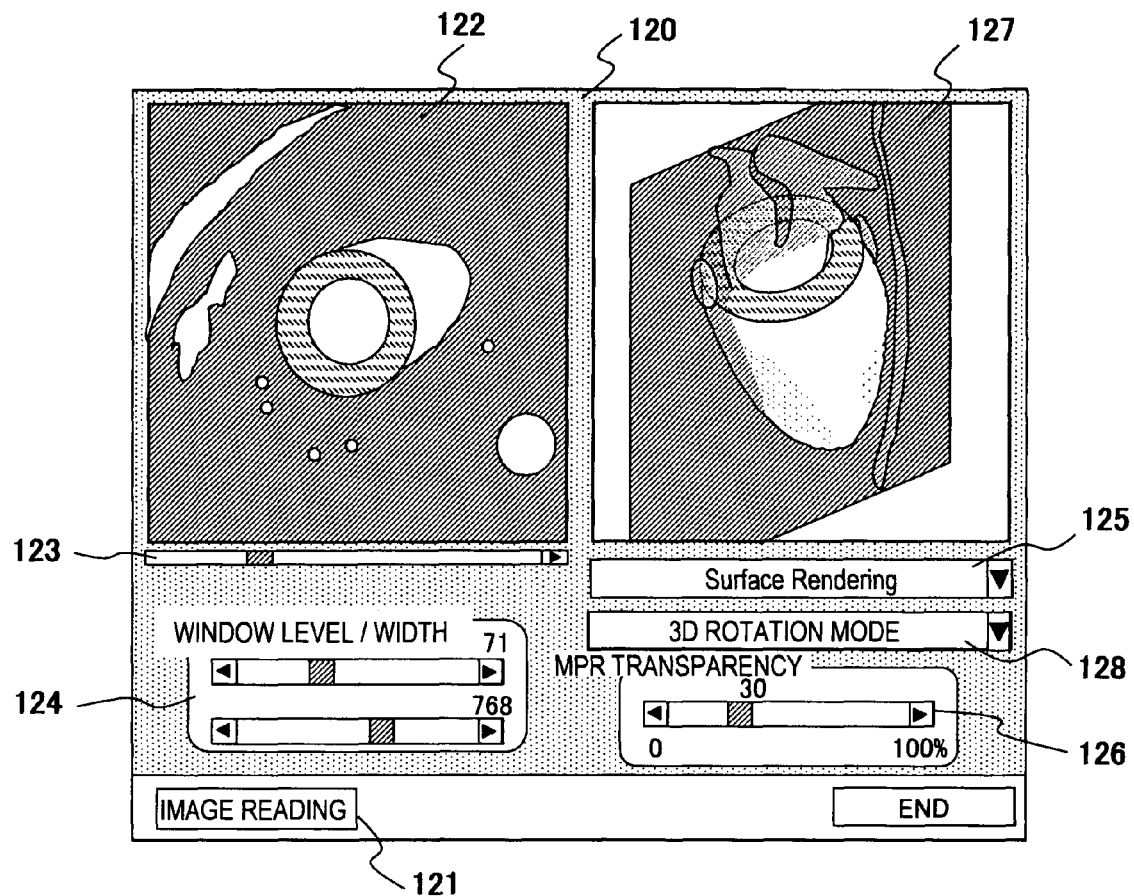
FIG. 12 is an example of GUI for implementing embodiment 3.
Figure 13:
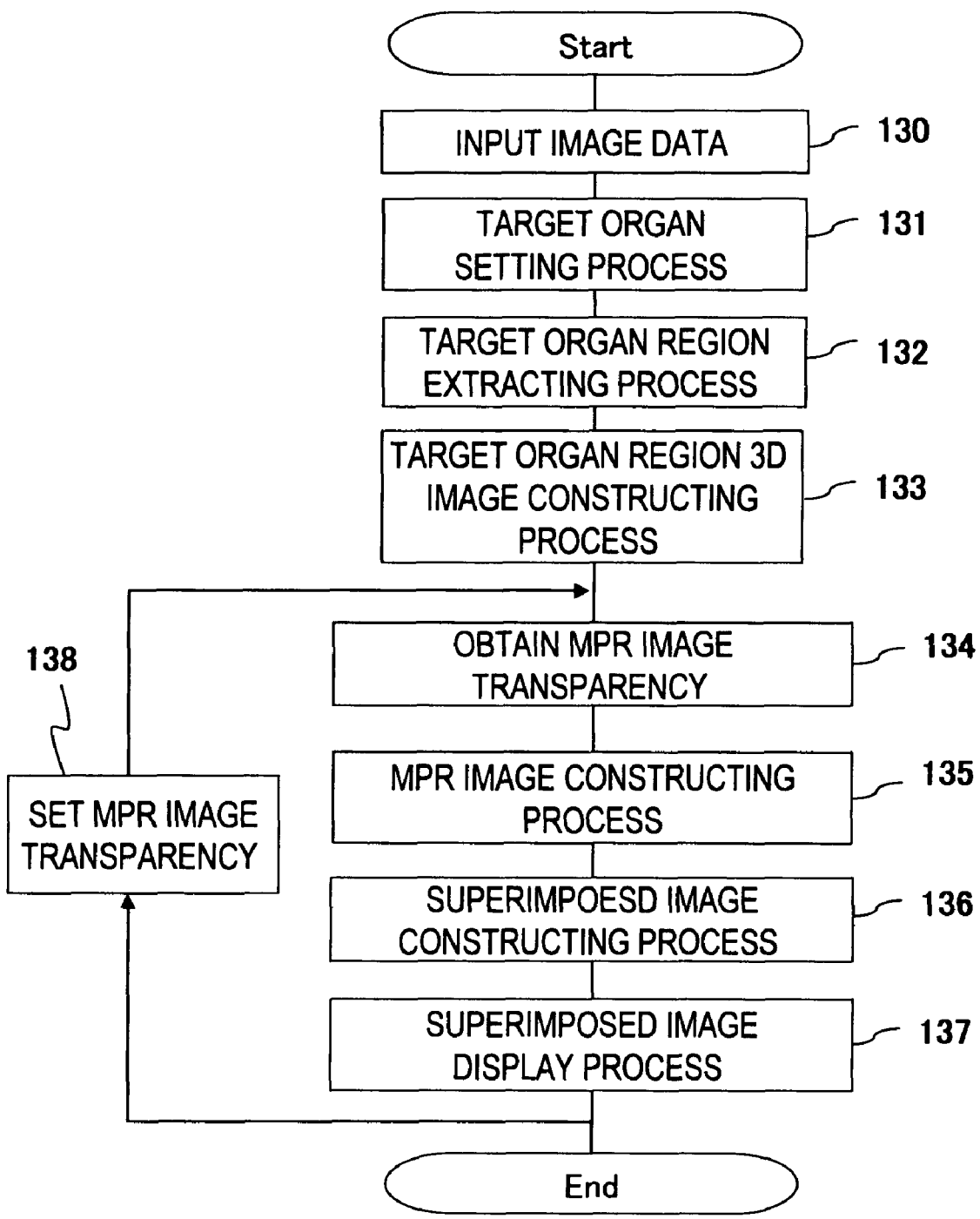
FIG. 13 is an example of a processing flow chart of embodiment 3.

The third embodiment of the present invention will now be described using the diagrams. An example of the GUI to carry out the present embodiment is shown in FIG. 12. The respective steps of FIG. 13 will be described below using the diagram.

(Step 130)

The operator inputs the medical tomogram group such as X-ray CT images or MRI images being imaged by X-ray CT apparatus or MRI apparatus, by pushing image read-in button 121 on GUI 120 using an input device such as mouse 16.

The inputted image is displayed on image display region 122. The slice of image to be displayed may be selected out of the inputted medical tomogram group at the discretion of the operator through operating slice-forwarding scroll bar 123 using an input device such as mouse 16 or keyboard 17. Also, the operator can display the inputted images with the arbitrary gradation through the operation of gradation conversion scroll bar 124 using an input device such as mouse 16 or keyboard 17.

(Step 131)

The operator specifies a target organ region on a medial tomogram image such as an X-ray CT image or MR image being displayed on image display region 122 of GUI 120 by operating an input device such as mouse 16.

(Step 132)

CPU 10 extracts the specified organ region using, for example, the region growing method.

(Step 133)

CPU 10 constructs a 3-dimensional image of the target organ region extracted in step 132, using the surface rendering method or volume rendering method. It may be set so that the operator can arbitrarily choose whether to use the surface rendering method or volume-rendering method by operating combo box 125 on GUI 120 using an input device such as mouse 16.

(Step 134)

CPU 10 acquires the value of transparency from transparency-setting scroll bar 126.

(Step 135)

CPU 10 constructs an MPR image that is cut at the cross-section with a discretional slope and has the discretional coordinate in the superimposed medical tomographic images as a center.

(Step 136)

Figure 14:
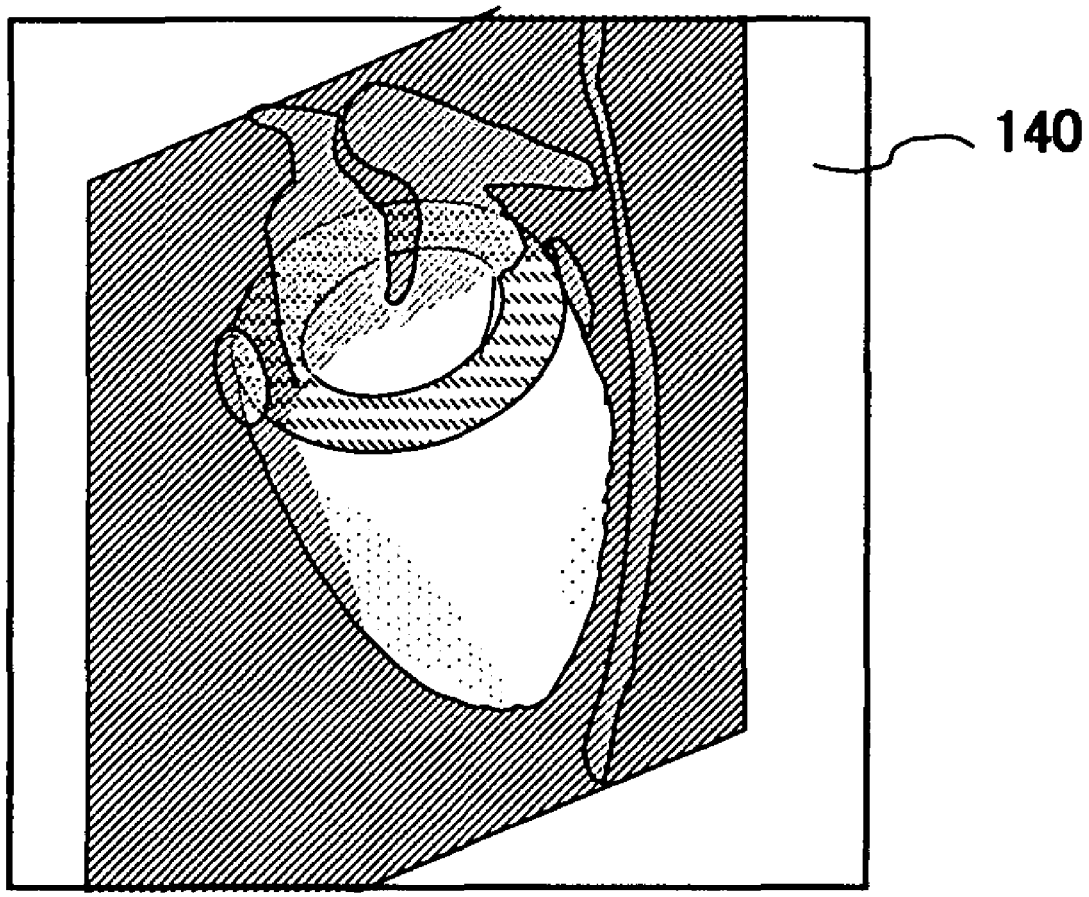
FIG. 14 is an example of a superimposed image of the 3-dimensional image and MPR image constructed in embodiment 3.

CPU 10 constructs a superimposed image of a 3-dimensional image of the target organ region and the MPR image. Then the coordinate is set so that the positional relationship between the 3-dimensional image and MPR image coincides with the actual positional relationship. Also, by superimposing the MPR image and translucently displaying using transparency obtained in step 134, the superimposed image turns out as seen in image 140 of FIG. 14. By such operation, the 3-dimensional image is translucently displayed and the MPR image is displayed in transparent state.

(Step 137)

CPU 10 displays the superimposed image of the constructed 3-dimensional image and MPR image on superimposed image display region 127 on GUI 120.

Here, it may be set so that the operator can freely change the display angle of the 3-dimensional image by dragging mouse 16 on superimposed image display region 127, or that the MPR image rotates while maintaining the positional relationship at the same time the 3-dimensional image rotates. Or, it may be set so that the operator rotates only the cross-section for constructing an MPR image while maintaining the angle of the 3-dimensional image by dragging mouse 16 on display region 127 of the superimposed image. When the cross-section rotates, the displayed MPR image naturally varies in compliance with the position of the cross-section. Alternatively, it may also be set so that the operator moves only the central position of the cross-section for constructing an MPR image while maintaining the angle of the 3-dimensional image and the cross-section for constructing MPR image by dragging mouse 16 on display region 127 of the superimposed image. The MPR image varies in compliance with the movement of the displayed MPR image.

As for the options to be operated using a mouse such as the rotation of the 3-dimensional image, the rotation of the cross-section for constructing an MPR image and the movement of the cross-section for constructing the MPR image, it may be set so that only one option can be carried out, or that the operator can choose to switch modes such as the rotation and can carry out all of the options. These modes may be selected in, for example, rotation mode combo box 128 on GUI 120.

(Step 138)

The operator may arbitrarily change transparency of the 3-dimensional image as necessary by operating transparency setting scroll bar 125 using an input device such as mouse 16 or keyboard 17 while observing the superimposed image displayed on superimposed image display region 127 on GUI 120. In 3-dimensional image construction process, step 134 is to proceed immediately when transparency of the 3-dimensional image is changed, and the new superimposed image is constructed.

Accordingly, information on both the 3-dimensional image set in translucent and the MPR image can be obtained simultaneously by superimposing them.

The Fourth Embodiment

Figure 15:
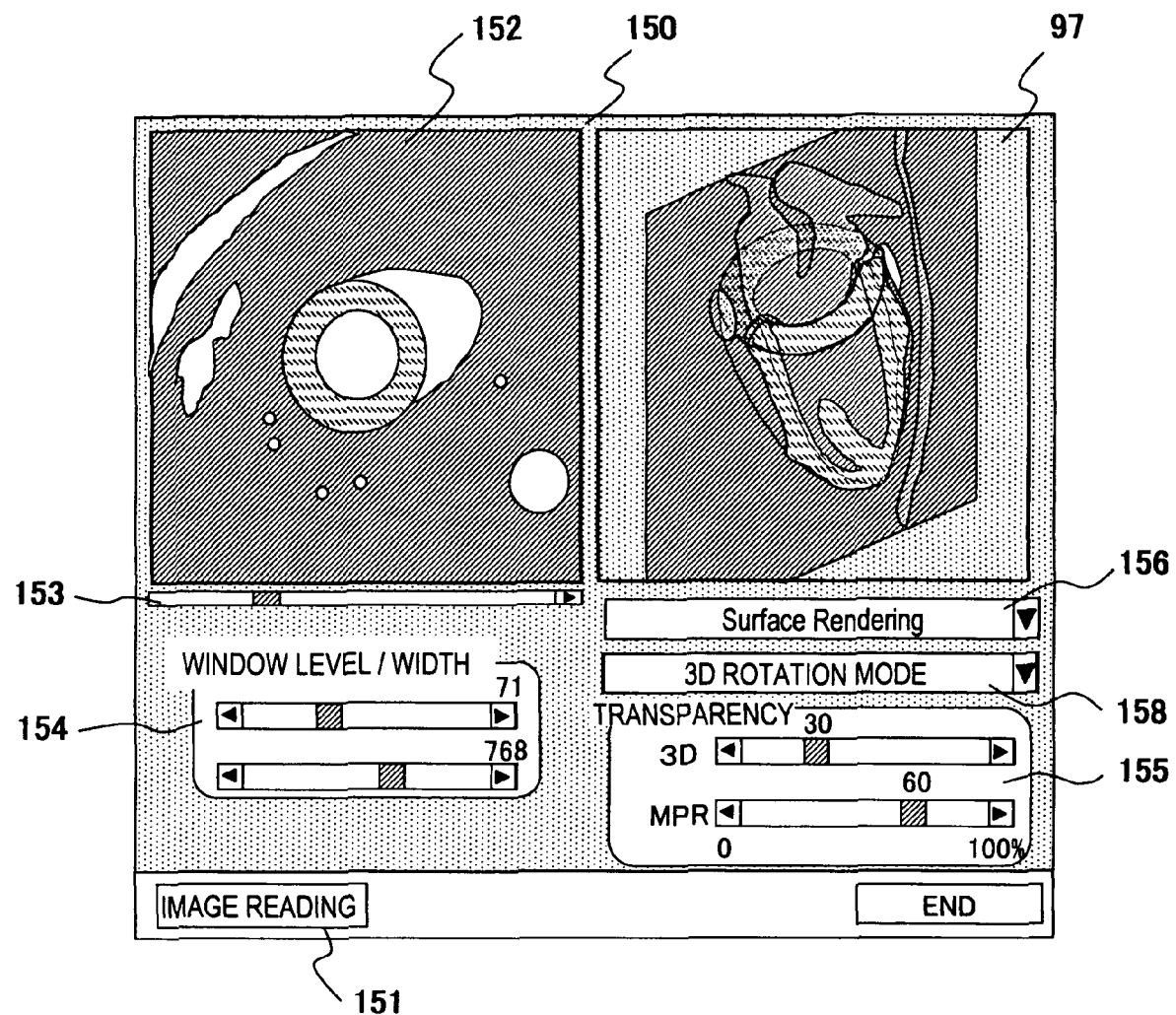
FIG. 15 is an example of GUI for implementing embodiment 4.
Figure 16:
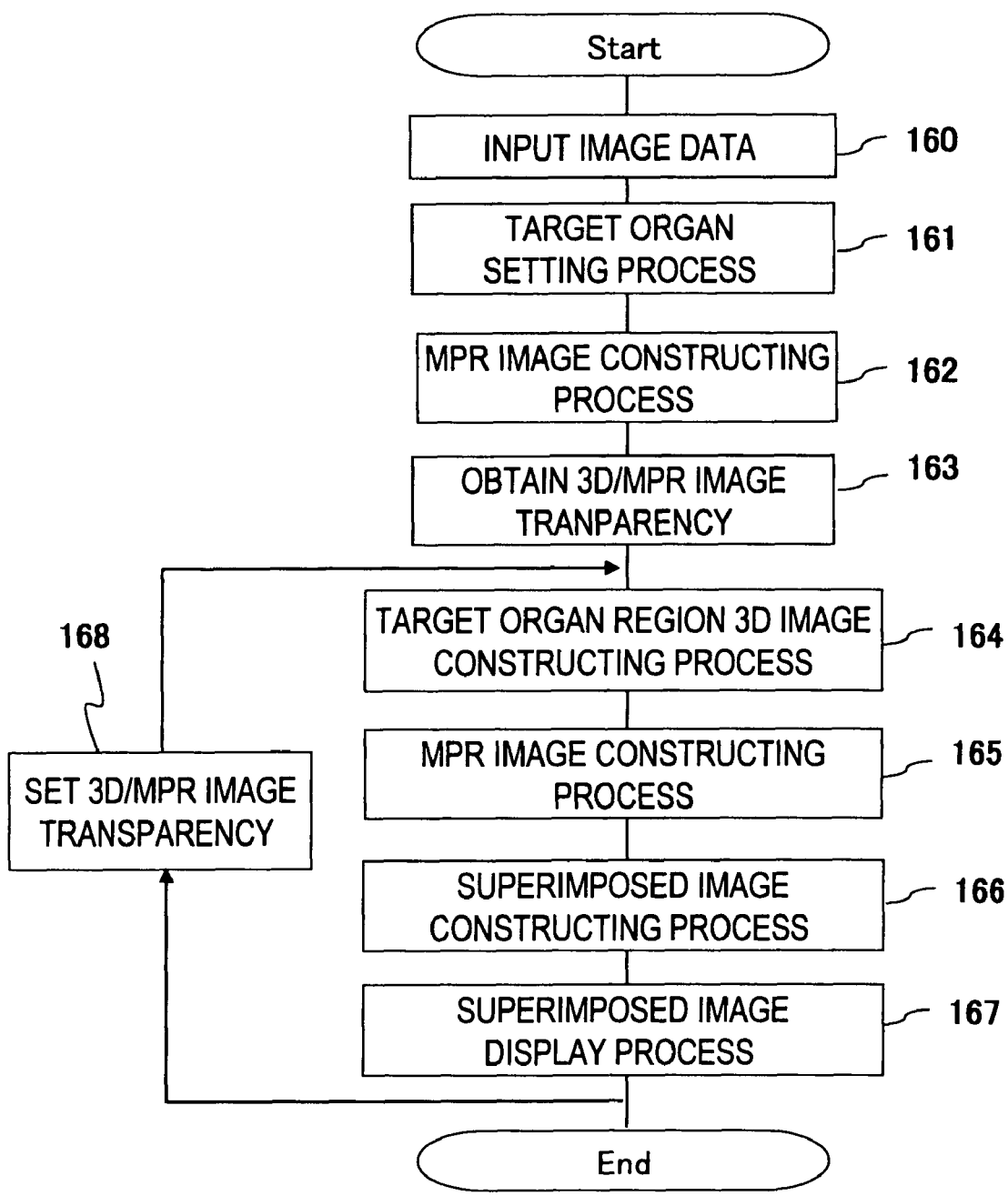
FIG. 16 is an example of a processing flow chart of embodiment 4.

The fourth embodiment of the present invention will now be described using the diagrams. An example of the GUI for carrying out the present embodiment is shown in FIG. 15. An example of the processing flow chart for the present embodiment is illustrated in FIG. 16. The respective steps of FIG. 16 will be described below using the diagram.

(Step 160)

The operator inputs a medical tomogram group such as X-ray CT images or MRI images being imaged by an X-ray CT apparatus or MRI apparatus, by pushing image read-in button 151 on GUI 150 using an input device such as mouse 16.

The inputted image is displayed on image display region 152. The slice of image to be displayed may be selected out of the inputted medical tomogram group at the discretion of the operator through operating slice-forwarding scroll bar 153 using an input device such as mouse 16 or keyboard 17. Also, the operator can display the inputted images with the arbitrary gradation through the operation of gradation conversion scroll bar 154 using an input device such as mouse 16 or keyboard 17.

(Step 161)

The operator specifies a target organ region on a medial tomogram image such as an X-ray CT image or MR image being displayed on image display region 152 of GUI 150 by operating an input device such as mouse 16.

(Step 162)

CPU 10 extracts the specified organ region using, for example, the region growing method.

(Step 163)

CPU 10 acquires transparency for the 3-dimensional image and the MPR image from transparency-setting scroll bar 155.

(Step 164)

CPU 10 constructs a 3-dimensional image of the target organ region extracted in step 152, using the surface rendering method or volume rendering method. It may be set so that the operator can arbitrarily choose whether to use the surface rendering method or volume-rendering method by operating combo box 156 on GUI 150 using an input device such as mouse 16.

(Step 165)

CPU 10 constructs an MPR image that is cut at the cross-section with a discretional slope and has the discretional coordinate in the superimposed medical tomographic images as a center.

(Step 166)

Figure 17:
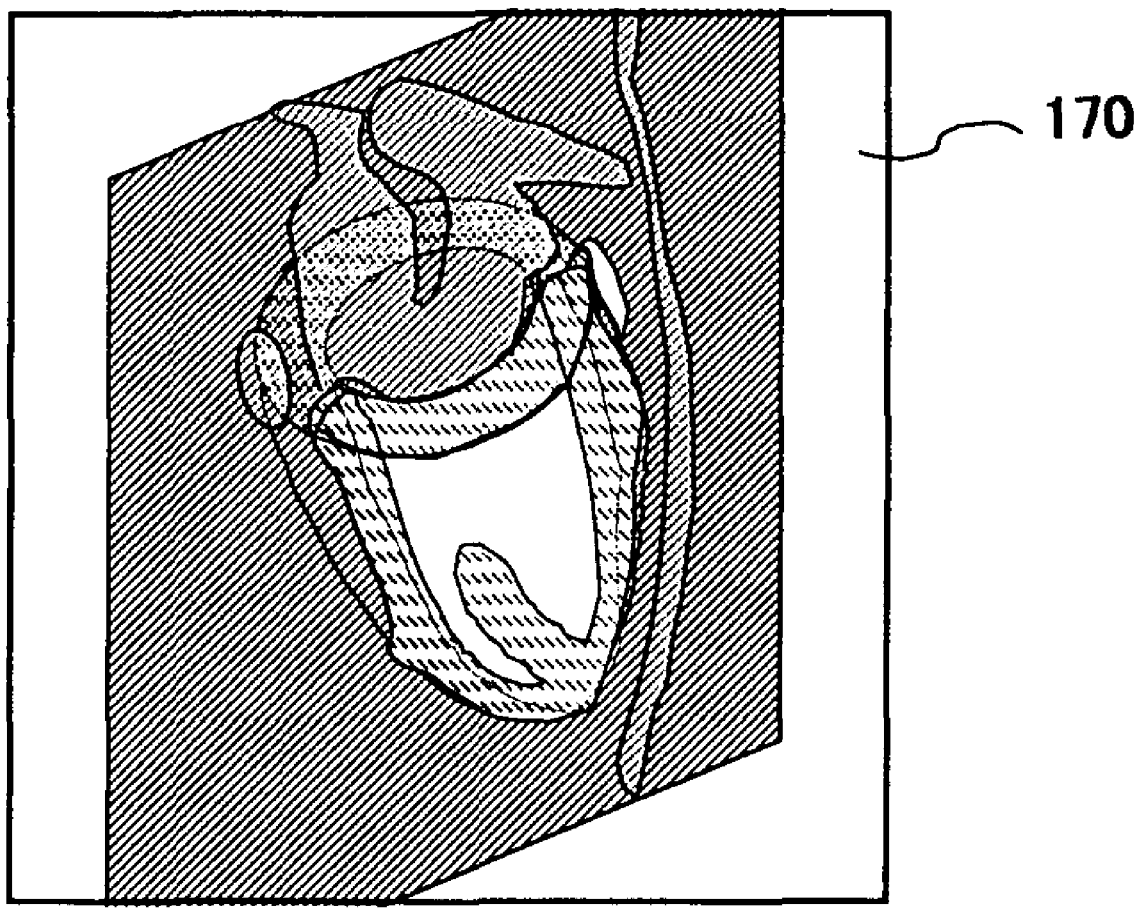
FIG. 17 is an example of a superimposing image of the 3-dimensional image and MPR image constructed in embodiment 3.

CPU 10 constructs a superimposed image of a 3-dimensional image of the target organ region and the MPR image. Then the coordinate is set so that the positional relationship between the 3-dimensional image and MPR image coincides with the actual positional relationship. Also, the 3-dimensional image and the MPR image are superimposed using transparency obtained in step 163. The superimposed image turns out as seen in image 170 of FIG. 17. By such operation, both the 3-dimensional image and the MPR image are translucently displayed.

(Step 167)

CPU 10 displays the superimposed image of the constructed 3-dimensional image and MPR image on superimposed image display region 157 on GUI 150.

Here, it may be set so that the operator can freely change the display angle of the 3-dimensional image by dragging mouse 16 on superimposed image display region 157, or that the MPR image rotates while maintaining the positional relationship at the same time the 3-dimensional image rotates. Or, it may be set so that the operator rotates only the cross-section for constructing an MPR image while maintaining the angle of the 3-dimensional image by dragging mouse 16 on display region 157 of the superimposed image. When the cross-section rotates, the MPR image being displayed naturally varies in compliance with the position of the cross-section. Alternatively, it may also be set so that the operator moves only the central position of the cross-section for constructing an MPR image while maintaining the angle of the 3-dimensional image and the cross-section for constructing MPR image by dragging mouse 16 on display region 157 of the superimposed image. The MPR image varies in compliance with the movement.

As for the options to be operated using a mouse such as the rotation of the 3-dimensional image, the rotation of the cross-section for constructing an MPR image and the movement of the cross-section for constructing the MPR image, it may be set so that only one option can be carried out, or that the operator can choose to switch the modes such as the rotation and can carry out all of the options. These modes may be set as selective in, for example, rotation mode combo box 158 on GUI 150.

(Step 168)

The operator may arbitrarily change transparency of the 3-dimensional image as necessary by operating transparency setting scroll bar 155 using an input device such as mouse 16 or keyboard 17 while observing the superimposed image displayed on superimposed image display region 157 on GUI 150. As soon as transparency is changed, the process after the 3-dimensional image construction process in step 164 is executed, and a new superimposed image is constructed.

Accordingly, the target for setting translucent state, that is 3-dimensional image or MPR image can be selected.

While the method for displaying the superimposed image by superimposing the 3-dimensional image and the cut cross-sectional image is described in embodiments 1~4, it may be set so that the cross-sectional image is displayed next to these superimposed images. Also, it can be set to select as to display only 3-dimensional image or to superimpose the images, by on/off switching.

Figure 18:
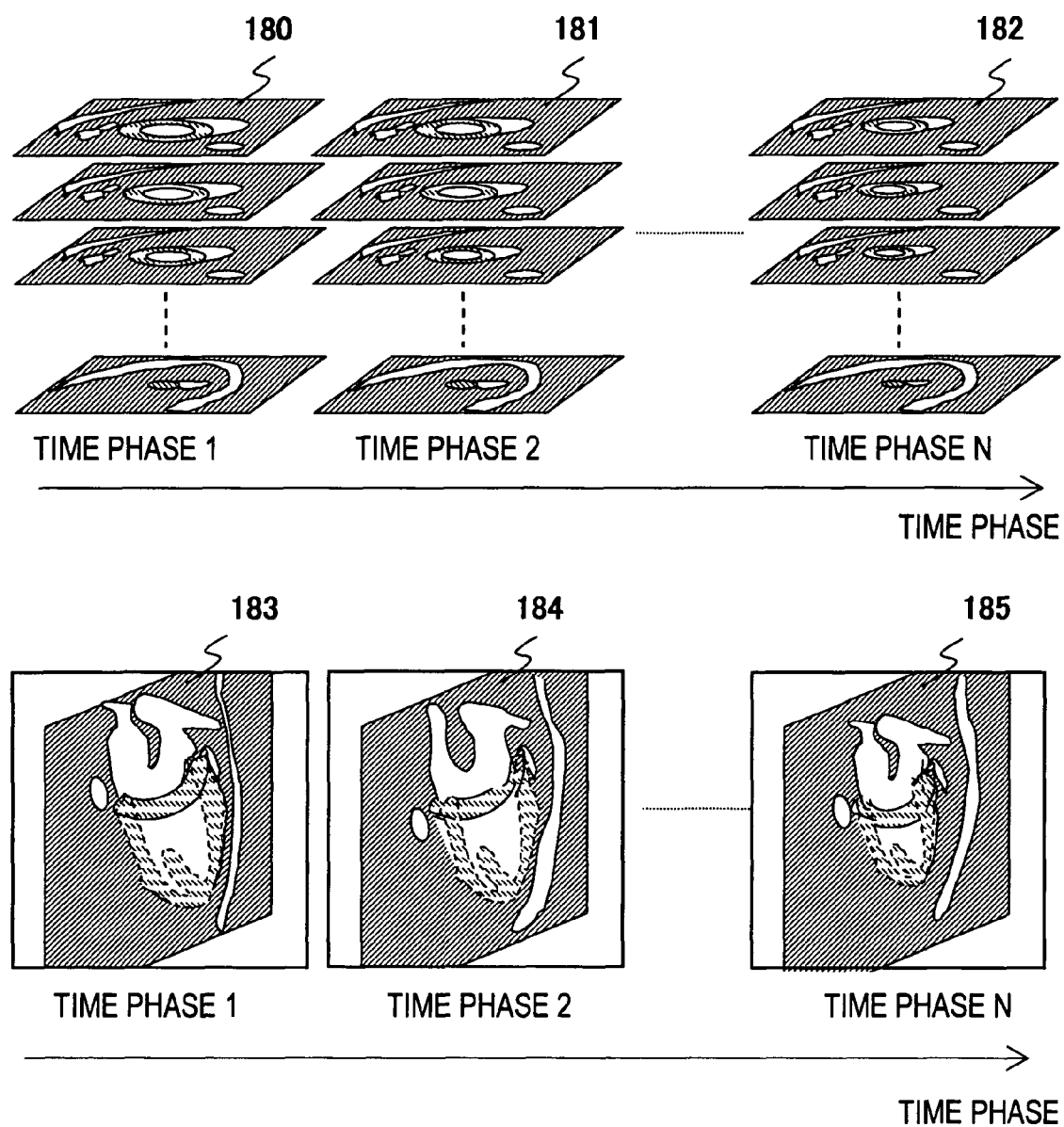
FIG. 18 is an example of cine-mode display of a superimposed image of the 3-dimensional image and MPR image.

While an example for superimposing the 3-dimensional image and MPR image as to the medical image for one time phase is described in embodiments 1~4, in relation to an organ with periodic motion such as a heart and there are a plurality of tomogram group for each time phase of the heart-beat being imaged, the superimposed images of the 3-dimensional image and MPR image described in embodiments 1~4 may be constructed and continuously displayed in cine-mode according to the progression of the time phase of the heartbeat as shown in images 183~185 of FIG. 18.

As for the concrete example shown in FIG. 18, a superimposed image of the 3-dimensional image corresponding to the cardiac diastole and the MPR image is constructed in time phase 1, a superimposed image of 3-dimensional image at cardiac systole and MPR image is constructed in time phase 2, and a superimposed image of a 3-dimensional image corresponding to the shrunk time period and MPR image is constructed in time phase 3.

While an example of citing a heart as observation target is described, an organ other than the cardiac muscle such as, for example, a blood vessel or lung may be the target.

INDUSTRIAL APPLICABILITY

The present invention provides a medical image display method, program and device capable of simultaneously displaying a 3-dimensional image including information on the target organ region and an MPR image including information on the surrounding organs of the target organ. This makes it possible to grasp the positional relationship of the target organ configuration and the surrounding organs thereof simultaneously.

Moreover, since only the target organ is displayed 3-dimensionally and the MPR image is used to display the surrounding organs, the calculation time can be shortened and the rotational display or movie display of the images can be executed at high speed.

Furthermore, by setting transparency to the 3-dimensional images or MPR images, it is possible to obtain information on the region hidden behind a 3-dimensional image or the region hidden in the back surface of an MPR image at the same time.

The invention claimed is:

1. A medical image display device comprising:
    tomogram input means for inputting a plurality of tomograms obtained by a medical imaging device;
    3-dimensional image construction means for constructing a 3-dimensional image by layering the tomograms inputted;
    arbitrary cross-section image construction means for cutting the 3-dimensional image at an arbitrary cross-section and constructing the cross-section image from the tomograms;
    superimposed image construction means for constructing a superimposed image of the 3-dimensional image and the arbitrary cross section image according to positional information on the tomogram; and
    display means for displaying the superimposed image thus constructed; and
    setting means for setting a display angle of at least one of (a) the 3-dimensional images and (b) the arbitrary cut cross-section image out of the superimposed image displayed by the display means.

2. The medical image display device according to claim 1, wherein:
    the 3-dimensional image construction means includes means for setting transparency to the constructed 3-dimensional image and constructs the 3-dimensional image having the set transparency; and
    the superimposed image construction means constructs the superimposed image of the 3-dimensional image having the set transparency and the arbitrary cut cross section image.

3. The medical image display device according to claim 2, wherein:
    the superimposed image construction means constructs a superimposed image in the case that transparency of the 3-dimensional image is set to be changed by the setting means; and
    the display means displays the superimposed image thus constructed.

4. The medical image display device according to claim 1, wherein:
    the arbitrary cut cross-section image construction means includes the means for setting transparency to the constructed arbitrary cut cross section image and constructs the arbitrary cut cross-sectional image having the set transparency; and
    the superimposed image construction means constructs the superimposed image of the 3-dimensional image and the arbitrary cut cross section image having the set transparency.

5. The medical image display device according to claim 4, wherein:
    the superimposed image construction means constructs the superimposed image in the case that transparency of the arbitrary cut cross section image is set to be changed by the setting means; and
    the display means displays the superimposed image thus constructed.

6. The medical image display device according to claim 1, including means for setting transparency to the 3-dimensional image and/or the arbitrary cut cross section image respectively constructed by the 3-dimensional image construction means or the arbitrary cut cross section image construction means, wherein:
    the 3-dimensional image construction means and the arbitrary cut cross section image construction means respectively construct a 3-dimenisoal image or an arbitrary cut cross section image having the set transparency, and
    the superimposed image construction means constructs a superimposed image of the 3-dimensional image having set transparency and the arbitrary cross sectional image having set transparency.

7. The medical image display device according to claim 6, which constructs the 3-dimensional image and the arbitrary cut cross section image in the case that transparency of the 3-dimensional image and the arbitrary cut cross section image is changed by transparency setting means, and constructs the superimposed image of the constructed 3-dimensional image and the arbitrary cut cross section image, wherein the display means displays the superimposed image thus constructed.

8. The medical image display device according to claim 1, wherein:
    the tomogram input means is for inputting a plurality of tomograms of each different time phase obtained by a medical imaging device;
    the 3-dimensional image construction means is for layering the plurality of tomograms of each different time phase inputted by the tomogram inputted means and constructing the 3-dimensional image of each different time phase;
    the arbitrary cut cross section image construction means is for cutting the 3-dimensional images of each different time phase at an arbitrary cross section and constructing the respective cut tomograms with different time phases from the plurality of tomograms of each different time phase;
    the superimposed image construction means is for constructing the superimposed image with respect to each different time phase of the 3-dimensional image of each different time phase and the arbitrary cut cross section image of each different time phase based on positional information of the plurality of tomograms of each different time phase; and
    the display means is for displaying the superimposed images thus constructed with respect to each different time phase.

9. The medical image display device according to claim 1, wherein the display means is for displaying the plurality of tomograms used for constructing the 3-dimensional image.

10. A medical image display method including:
    a tomogram input step for inputting a plurality of tomograms obtained by a medical imaging device;
    a 3-dimensional image construction step for constructing a 3-dimensional image by layering the plurality of inputted tomograms;
    an arbitrary cut cross section image construction step for cutting the 3-dimensional image at an arbitrary cross section and constructing the cut cross section image from the plurality of tomograms;
    a superimposed image construction step for constructing a superimposed image of the 3-dimensional image and the arbitrary cut cross section image based on positional information of the tomograms; and
    a display step for displaying the superimposed image thus constructed; and
    a setting step for setting a display angle of at least one of (a) the 3-dimensional images and (b) the arbitrary cut cross section image out of the superimposed images displayed by the display step.

11. The medical image display method according to claim 10, which includes a step for setting transparency to the 3-dimensional images constructed by the 3-dimensional image construction step and/or the arbitrary cut cross section image constructed by the arbitrary cut cross section image construction step, and constructs the 3-dimensional images and/or the arbitrary cut cross section image having transparency set by the transparency setting step, wherein the superimposed image construction step constructs the superimposed image of the 3-dimensional image and the arbitrary cut cross section image.

12. The medical image display method according to claim 11, which constructs the 3-dimensional image and the arbitrary cut cross section image in the case that transparency of the 3-dimensional images and/or the arbitrary cut cross section image is set to be changed by the transparency setting step, wherein:
the superimposed image construction step is for constructing the superimposed image from the constructed 3-dimensional image and the arbitrary cut cross section image; and
the display step is for displaying the superimposed image thus constructed.

13. The medical image display method according to claim 10, wherein:
the tomogram input step is for inputting a plurality of tomograms of each different time phase obtained by a medical imaging device;
the 3-dimensional image construction step is for layering the inputted plurality of tomograms of each different time phase and constructing a 3-dimensional image of each different time phase;
the arbitrary cut cross section image construction step is for cutting the 3-dimensional image of each different time phase at an arbitrary cross section, and constructing the respectively cut cross section images of each different time phase from the plurality of tomograms of each different time phase;
the superimposed image construction step is for constructing a superimposed image with respect to each different time phase of the 3-dimensional image of each different time phase and the arbitrary cut cross section image of each different time phase based on positional information of the plurality of tomograms of each different time phase; and
the display step is for displaying the superimposed image thus constructed of each different time phase.

14. A non-transitory, computer readable medium tangibly embodying a medical image display program executable by a computer to perform a method including:
a tomogram input process for inputting a plurality of tomograms obtained by a medical imaging device;
a 3-dimensional image construction process for constructing a 3-dimensional image by layering the plurality of tomograms inputted;
an arbitrary cut cross section image construction process for cutting the 3-dimensional image at an arbitrary cross section and constructing the cut cross section image from the plurality of tomograms;
a superimposed image construction process for constructing a superimposed image of the 3-dimensional image and the arbitrary cut cross section image based on positional information of the tomograms; and
a display process for displaying the superimposed image thus constructed; and
a setting process for setting a display angle of at least one of (a) the 3-dimensional images and (b) the arbitrary cut cross section image out of the superimposed images displayed by the display process.

15. The non-transitory, computer readable medium including the medical image display program to perform the method according to claim 14, which includes a process for setting transparency to the 3-dimensional images constructed by the 3-dimensional image construction process and/or the arbitrary cut cross section image constructed by the arbitrary cut cross section image construction process, and constructs the 3-dimensional image and/or the arbitrary cut cross section image having transparency set by the transparency setting process, wherein the superimposed image construction process constructs the superimposed image of the 3-dimensional image and the arbitrary cut cross section image.

16. The non-transitory, computer readable medium including the medical image display program to perform the method according to claim 15, which constructs the 3-dimensional image and the arbitrary cut cross section image in the case that transparency of the 3-dimensional images and/or the arbitrary cut cross section image is set to be changed by the transparency setting process, wherein:
the superimposed image construction process is for constructing the superimposed image from these constructed 3-dimensional images and the arbitrary cut cross section image; and
the display process is for displaying the superimposed image thus constructed.

17. The non-transitory, computer readable medium including the medical image display program to perform the method according to claim 14, wherein:
the tomogram input process is for inputting a plurality of tomograms of each different time phase obtained by a medical imaging device;
the 3-dimensional image construction process is for layering the inputted plurality of tomograms of each different time phase and constructing a 3-dimensional image of each different time phase;
the arbitrary cut cross section image construction process is for cutting the 3-dimensional image of each different time phase at an arbitrary cross section, and constructing the respectively cut cross section image of each different time phase from the plurality of tomograms of each different time phase;
the superimposed image construction process is for constructing a superimposed image with respect to each different time phase of the 3-dimensional image of each different time phase and the arbitrary cut cross section image of each different time phase based on positional information of the plurality of tomograms of each different time phase; and
the display process is for displaying the superimposed image thus constructed of each different time phase.

* * * * *